United States Patent [19]
Reetz et al.

[11] Patent Number: 6,087,481
[45] Date of Patent: Jul. 11, 2000

[54] OLEFIN HYDROFORMYLATION PROCESS IN A TWO-PHASE SYSTEM

[75] Inventors: Manfred T. Reetz, Mülheim an der Ruhr; Siegfried Waldvogel, Münster, both of Germany

[73] Assignee: Studiengesellschaft Kohle mbH, Mulheim an der Ruhr, Germany

[21] Appl. No.: 09/230,575

[22] PCT Filed: Jul. 29, 1997

[86] PCT No.: PCT/EP97/04117

§ 371 Date: Jan. 27, 1999

§ 102(e) Date: Jan. 27, 1999

[87] PCT Pub. No.: WO98/05618

PCT Pub. Date: Feb. 12, 1998

[30] Foreign Application Priority Data

Aug. 2, 1996 [DE] Germany .......................... 196 31 322

[51] Int. Cl.⁷ .......................... C08B 37/16; C07C 45/50
[52] U.S. Cl. ...................... 536/18.7; 536/120; 536/123.1; 568/451; 568/454

[58] Field of Search ..................... 568/451, 454; 536/18.7, 120, 123.1

[56] References Cited

FOREIGN PATENT DOCUMENTS 96 222 67   7/1996   WIPO .

OTHER PUBLICATIONS

E. Monflier et al. "A Further Breakthrough . . . Catalysts", Tetrahedron Letters, Bd, 36, Nr. 52, Dec. 25, 1995, pp. 9481–9484.

*Primary Examiner*—Sreeni Padmanabhan
*Attorney, Agent, or Firm*—Norris, McLaughlin & Marcus, P.A.

[57] ABSTRACT

The present invention relates to a process for the hydroformylation of terminal and internal olefins in a two-phase system using novel metal catalysts. The two-phase system consists of an aqueous and an organic phase. The metals belong to group VIII of the Periodic Table, e.g., Rh, Ru, Ir, Co or Pd. The ligands for the metals are novel phosphane-modified β-cyclodextrins which are water-soluble.

4 Claims, No Drawings

OLEFIN HYDROFORMYLATION PROCESS IN A TWO-PHASE SYSTEM

This is the U.S. National Stage Application of PCT/EP97/04117 filed Jul. 29, 1997.

FIELD OF THE INVENTION

The present invention relates to a process for the hydroformylation of terminal and internal olefins in a two-phase system using novel metal catalysts. The two-phase system consists of an aqueous and an organic phase. The metals belong to group VIII of the Periodic Table, e.g., Rh, Ru, Ir, Co or Pd. The ligands for the metals are novel phosphane-modified β-cyclodextrins which are water-soluble.

The aldehydes formed in the hydroformylation are industrially useful compounds which are either used directly, e.g., as aromatic principles, or as intermediates for the production of other classes of substances, as in the preparation of solvents, detergents, perfumes, pharmaceutical agents or plasticizers [K. Weissermel, H. J. Arpe, Industrial Organic Chemistry, VCH, Weinheim, 1993].

BACKGROUND OF THE INVENTION

Commercially, the cobalt catalysts introduced by Roelen, e.g., $Co_2(CO)_8$, are used at 150–180° C./150–200 atm, conditions which lead to side-reactions, such as hydrogenation, isomerization and aldehyde condensation. In the so-called low pressure oxo process, rhodium complexes which are soluble in organic solvents, such as $HRh(CO)(PPh_3)_3$, are used as catalysts, working at 90–110° C./20 atm and thus yielding less undesirable side-products. This process as well as other homogeneously catalyzed hydroformylations are mainly used for the production of butyric aldehyde and other low-boiling aldehydes. However, with homologous or higher-boiling aldehydes, the distillative separation from the catalyst is problematic [G. W. Parshall, S. D. Itell, Homogeneous Catalysis, Wiley, New York, 1992]. For this reason, attempts are being made in the industry world-wide to perform hydroformylations in a two-phase system [B. Cornils, in New Syntheses with Carbon Monoxide (J. Falbe, ed.), Springer Publishers, New York, 1980; B. Cornils, E. Wiebus, Chemtech. 1995, 33]. To this end, water-soluble phosphanes, e.g., $P(C_6H_4SO_3Na)_3$, are used as ligands for the rhodium (TPPTS-Rh system). The Rh catalyst is present in the aqueous phase whereas the olefin and the product (aldehyde) are present in the organic phase. In this way, Hoechst/Rhone-Poulenc produce n-butyric aldehyde from propene [B. Cornils, E. Wiebus, Chem. Ing. Tech. 66 (1994), 916; W. A. Herrmann et al., J. Mol. Catal. 97 (1995), 65]. Unfortunately, this simple process is limited to ethylene and propene, which have a water solubility which, although low, is yet sufficiently high to be reacted in the aqueous or catalyst-containing phase. Homologous olefins, such as n-hexene or n-octene, are virtually not or but poorly reacted in this system. Therefore, there have been many attempts to solve this problem, e.g., using surfactants or phase-transfer catalysts, especially ligands or solvents, but only with limited success as recently reviewed by E. Monflier [Angew. Chem. 107 (1995), 2450; Tetrahedron Lett. 36 (1995), 9481]. An improvement is described by E. Monflier [supra] according to which β-cyclodextrin derivatives (β-CD derivatives) are added to the two-phase system, serving as solubilizers. In the case of longer-chain olefins, such as 1-octene or 1-decene, the activity of the catalyst system is increased thereby by a maximum of about 10fold so that reasonable yields of the corresponding aldehydes are obtained, i.e., with n/iso ratios of about 2:1. However, the chemical selectivity is only 85–90% as a rule, i.e., 10–15% of side-products is obtained. Internal (i.e., non-terminal) olefins, such as 5-decene, are virtually not hydroformylated at all (only 3% conversion), i.e., the catalyst system is not very active. In addition, a great disadvantage is the fact that a large excess of β-cyclodextrin derivative is necessary; typically, the ratio of Rh:P $(C_6H_4SO_3Na)_3$:β-cyclodextrin derivative is about 1:8:14. The advantage of a moderate increase in activity by the use of CD derivatives is relativated in view of the disadvantages mentioned.

DETAILED DESCRIPTION OF THE INVENTION

The present invention involves a two-phase system ($H_2O$/organic phase) with a water-soluble catalyst which enables the smooth hydroforosylation of a wide variety of terminal and internal olefins with high selectivity (>99%), i.e., under surprisingly mild conditions. The catalyst system employed is surprisingly active. Thus, the catalyst activity in the hydroformylation of longer-chain 1-olefins, such as 1-octene, is about 150 times higher than that obtained in the known TPPTS-Rh system.

It is known that 1) β-cyclodextrin (β-CD) and many β-CD derivatives are water-soluble, and 2) such compounds are efficient host molecules which can reversibly trap or bind aliphatic and aromatic hydrocarbons in their hydrophobic inner cavities. If the β-CD contains a metal-bearing diphosphane, the olefins to be hydroformylated present in the organic phase can be trapped by the β-CD and spontaneously catalytically reacted.

The phosphane ligands synthesized according to the present invention belong to one of two classes: type I with free hydroxy groups, and type II with fully or partially alkylated hydroxy groups.

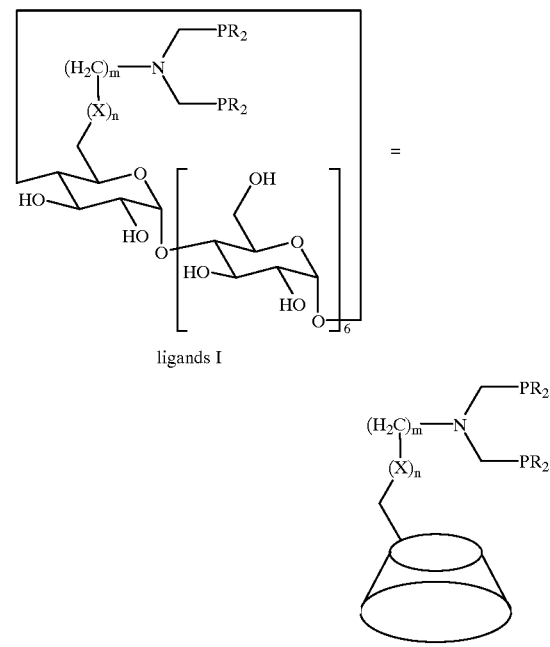

ligands I

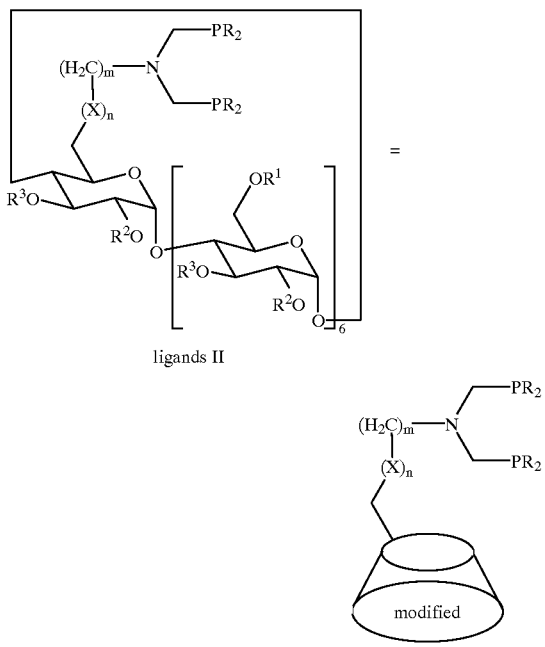

ligands II

From the formula representations I/II, it can be seen that a chelating diphosphane is linked to a β-CD through a spacer. In the simplest case, the spacer is very short, i.e., n=m=0. Such a ligand is often preferred. It is also possible, however, that X is a heteroatom, such as oxygen, sulfur or nitrogen (as an NR' fragment with R'=H, alkyl, aryl), n being 1 in these cases. The length of the remaining part of the spacer can be conveniently varied, e.g., m=0–6, preferably m=2–4. The R residues are aliphatic, such as ethyl, isopropyl or cyclohexyl, or preferably aromatic, such as phenyl or naphthyl, or substituted members, such as o-, m- or p-methyl, o-, m- or p-chloro, o-, m- or p-amino, or preferably o-, m- or p-$SO_3Na$ derivatives.

The residues $R^1$, $R^2$ and $R^3$ in the β-CD portion of the ligands II are alkyl residues, especially:

$R^1=R^2=R^3=CH_3$, $CH_2=CHCH_2$, $C_6H_5CH_2$, $HOCH_2CH(OH)CH_2$, $CH_3CH(OH)CH_2$; or $R^1=CH_3$, $CH_2=CHCH_2$, $C_6H_5CH_2$, $HOCH_2CH(OH)CH_2$, $CH_3CH(OH)CH_2$, $R^2=R^3=H$; or $R^1=H$, $R^2=R^3=CH_3$, $CH_2=CHCH_2$, $C_6H_5CH_2$, $HOCH_2CH(OH)CH_2$, $CH_3CH(OH)CH_2$; or $R^1=R^3=H$, $R^2=CH_3$, $CH_2=CHCH_2$, $C_6H_5CH_2$, $HOCH_2CH(OH)CH_2$, $CH_3CH(OH)CH_2$; or $R^1=R^2=CH_3$, $CH_2=CHCH_2$, $C_6H_5CH_2$, $HOCH_2CH(OH)CH_2$, $CH_3CH(OH)CH_2$, $R^3=H$.

To form the metal catalysts or precatalysts, the ligands are reacted with salts of metals of group VIII of the Periodic Table, especially salts of Rh, Ru, Ir, Co or Pd, preferably rhodium salts. $Rh(COD)_2BF_4$ is typically employed. One approach is to isolate and characterize the metal complexes formed and only then to employ them in the hydroformylation, another is to choose an in-situ reaction mode in which the ligand and metal salt are simply added to the reaction mixture.

The hydroformylation is performed in a two-phase system which comprises an organic phase and an aqueous phase containing the catalyst. The organic phase consists of an olefin to be reacted or of the olefin and an inert solvent, such as toluene or diethyl ether. Preferably, no organic solvent is used, i.e., the organic phase is the olefin itself. Small amounts of an additive in the form of a polar solvent, such as dimethylformamide, are optionally added to the aqueous phase.

To perform the hydroformylation, the two-phase system in a closed reaction vessel is pressurized with a mixture of CO and $H_2$, usually in a 1:1 ratio. The pressure during the hydroformylation can be varied from 1 to 300 atm, preferably in a range of from 20 to 100 atm. A range of temperatures of from 50° C. to 120° C. can be selected, the temperature preferably being between 60° C. and 80° C.

In the hydroformylation of t-alkenes, internal alkenes, 1,1-disubstituted alkenes and trisubstituted alkenes, the two-phase catalyst system according to the invention is significantly more active than the conventional two-phase system using water-soluble $P(C_6H_4SO_3Na)_3$ and Rh salts (cf. Hoechst/Rhone-Poulenc TPPTS-Rh system). For example, whereas 1-octene is virtually not hydroformylated at all with the latter catalyst system, a complete conversion with >99% selectivity can be achieved with Rh complexes of the β-CD modified ligands under comparable conditions (80° C./18 h/50 atm). The increase in catalyst activity when the two-phase catalyst system according to the invention is used instead of the TPPTS-Rh two-phase system is by a factor of more than 150. Surprisingly, even arrantly unreactive olefins, such as cis- or trans-3-hexene, and even trisubstituted alkenes, such as 1-methylcyclopentene, undergo smooth hydroformylations with the two-phase catalyst system according to the invention.

To synthesize the ligands, β-cyclodextrin is first selectively converted to the mono(6-O-p-toluenesulfonyl)-β-cyclodextrin known from the literature. The O-tosyl groups are displaced by a heteroatom through nucleophilic substitution. After the corresponding primary amines have been obtained, they are reacted with $(HOCH_2)_2P^+R_2X^-$ in a known manner to form the desired β-CD modified diphosphane ligands of types I and II.

In addition to the simple preparation of the ligands and the high catalyst activity and selectivity, the simple recovery of the catalyst in the form of the aqueous phase is another advantage.

EXPERIMENTAL DATA

EXAMPLE 1

$6^A$-N,N-Bis(diphenylphosphinomethyl)amino-$6^A$-desoxy-β-cyclodextrin

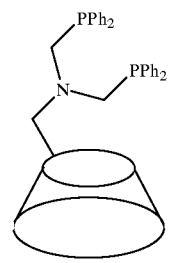

6-Desoxy-6-p-toluenesuifonyl-β-cyclodextrin:

This is obtained by direct tosylation in water (500 g of cyclodextrin in 3200 ml of water) with sodium hydroxide as the base and p-tosyl chloride. The reaction is performed at room temperature in open vessels. Small amounts of acetone are used to introduce the tosyl chloride. Precipitation is effected in the cold (0° C.), recrystallization from w water yields the product in 8% yield with a n HPLC purity of >94%.

When less water is used (2500 ml), 28% of product can be obtained from the recrystallization. The mixture of products thus obtained contains about 85% of 6-desoxy-6-p-toluenesulfonyl-β-cyclodextrin, the rest being unfunctionalized β-cyclodextrin.

$6^A$-Azido-$6^A$-desoxy-β-cyclodextrin:

This is obtained by nucleophilic substitution of 6-desoxy-6-p-toluenesulfonyl-β-cyclodextrin with N,N,N',N'-tetramethylguanidinium azide in DMF (90° C., 48 h). Precipitation is effected with acetone. Recrystallization from ethanol/water yields colorless crystals in 92% yield and an HPLC purity of >93%.

IR: v/cm$^{-1}$ (KBr): 2105 (ss, $N_3$)

$6^A$-Amino-$6^A$-desoxy-β-cyclodextrin:

This is obtained by catalytic reduction of $6^A$-azido-$6^A$-desoxy-β-cyclodextrin with platium dioxide (0.5%) and molecular hydrogen (1 atm). Water serves as the solvent (25° C., 8 h). The reaction is monitored by IR. The processing yields a slightly greyish power in 79% yield.

$6^A$-N,N-Bis(diphenylphosphinomethyl)amino-$6^A$-desoxy-β-cyclodexetrin:

1.5 g (5.3 mmol) of bis(hydroxymethyl) diphenylphosphonium chloride and 2.8 g (2.4 mmol) of $6^A$-amino-$6^A$-desoxy-β-cyclodextrin are dissolved in a mixture of 15 ml of water and 30 ml of methanol. After the addition of 1.3 ml (9.4 mmol) of triethylamine, mixture becomes cloudy. It is then refluxed for two hours. After cooling the greaish, 40 ml of water is added, and the mixture is allowed to stand at 0° C. for 18 hours. The suspension is syphoned onto an inert gas frit. The precipitate is washed twice with 10 ml of water and then with 20 ml of acetone. The residue is dried under high vacuum. For purification, the residue is recrystallized from methanol/benzene. The supernatant is decanted, and the solid is dried at 50° C. under diffusion pump vacuum. Yield: 3.35 g (2.1 mmol), 91%. $^{31}$P NMR (80 MHz, $d_6$-DMSO): δ=−27.1 ppm. MS (FAB/pos., matrix: glycerol): m/z=1530 [M+H]$^+$, 1344 [M−PPh$_2$]$^+$, 1158 [M−2PPh$_2$]$^+$. MS (FAB/neg., matrix: glycerol): m/z= 1528 [M−H]$^−$, 40% (for a detailed NMR study, see Example 2).

EA: $C_{68}H_{93}N_1P_2O_{34}.0.5C_6H_6$: MW (1568.521)

| calc.: | C 54.32 | H 6.17 | N 0.89 | P 3.95 |
| found: | C 54.16 | H 6.07 | N 0.73 | P 3.83 |

EXAMPLE 2

S-(2-N,N-Bis(diphenylphosphinomethyl) aminoethyl)-$6^A$-desoxy-$6^A$-thio-β-cyclodextrin

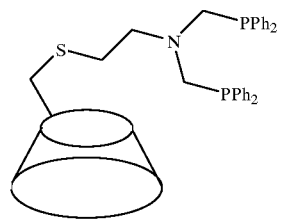

S-(2-Aminoethyl)-$6^A$-desoxy-$6^A$-thio-β-cyclodextrin:

The phthalimido protected compound is obtained by nucleophilic substitution of 6-desoxy-6-p-toluenesulfonyl-β-cyclodextrin with N-(2-mercapto)ethylphthalimide and cesium carbonate as a base. DMF is used as the solvent (80° C., 24 h). Hydrazinolysis and precipitation with absolute ethanol yield a raw product which is purified by recrystallization from methanol/water. Yield: 76% (based on the cyclodextrin tosylate employed).

S-(2-N,N-Bis(diphenylphosphinomethyl)aminoethyl)-$6^A$-desoxy-$6^A$-thio-β-cyclodextrin:

7.1 g (25 mmol) of bis(hydroxymethyl) diphenylphosphonium chloride and 10 g (8.3 mmol) of S-(2-aminoethyl)-$6^A$-desoxy-$6^A$-thio-β-cyclodextrin are dissolved in a mixture of 60 ml of water, 10 ml of benzene and 150 ml of methanol. After the addition of 3.4 ml (24.5 mmol) of triethylamine, the mixture becomes cloudy. It is then refluxed for two hours. A white solid precipitates upon cooling. The reaction mixture is decanted, and the residue is dried under high vacuum at 50° C. For purification, the residue is recrystallized from methanol/benzene. The polycrystalline solid is isolated and dried at 50° C. under diffusion pump vacuum. Yield: 9.72 g (6.15 mmol), 73% (based on the cyclodextrin tosylate employed). $^{31}$P NMR (100 MHz, $d_6$-DMSO): δ=−27.40 ppm. MS (ESI/pos. in MeOH, $H_2O$): m/z=1590 ([M+H]$^+$, 100%), 1392 ([M+H—$CH_2PPh_2$]$^+$, 60%).

EA: $C_{70}H_{97}N_1O_{34}P_2S_1.0.5C_6H_6$: MW (1628.532)

| calc.: | C 53.79 | H 6.19 | N 0.86 | P 3.80 |
| found: | C 53.69 | H 6.04 | N 1.05 | P 3.63 |

A detailed NMR study was made as an illustrative example of all derivatives from Examples 1–9. The studies were performed on a Bruker DMX-600.

Example 2

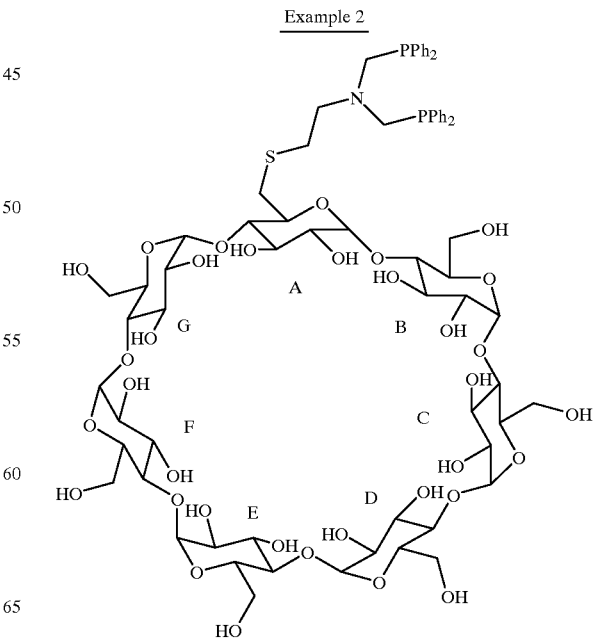

7

-continued

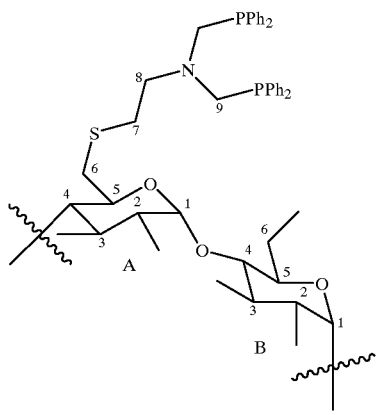

$^1$H NMR signals (600 MHz, δ in ppm, in $d_5$-pyridine)

| Fragment | H-1 | H-2 | H-3 | H-4 | H-5 | H-6 | |
|---|---|---|---|---|---|---|---|
| Ring A | 5.571 | 4.170 | 4.778 | 4.251 | 4.697 | 3.571 | 3.449 |
| Ring B | 5.703 | 4.149 | 4.810 | 4.217 | * | * | |
| Ring C | 5.698 | 4.160 | 4.825 | 4.331 | * | * | |
| Ring D | 5.692 | 4.154 | 4.816 | 4.312 | * | * | |
| Ring E | 5.693 | 4.151 | 4.817 | 4.324 | * | * | |
| Ring F | 5.672 | 4.159 | 4.823 | 4.323 | 4.545 | 4.509 | 4.475 |
| Ring G | 5.682 | 4.155 | 4.783 | 4.215 | 4.507 | 4.521 | 4.429 |

*non-resolvable multiplet between 4.41 and 4.6

| Fragment | H-7 | H-8 | H-9 |
|---|---|---|---|
| side chain | 3.058 | 3.382 | 3.805 |

C NMR signals (150 MHz, δ in ppm, in $d_5$-pyridine)

| Fragment | C-1 | C-2 | C-3 | C-4 | C-5 | C-6 |
|---|---|---|---|---|---|---|
| Ring A | 103.84 | 74.28 | 74.44 | 85.71 | 73.29 | 34.42 |
| Ring B | 104.01 | 74.41 | 74.76 | 83.67 | 73.98 | 61.80 |
| Ring C | 104.10 | 74.44 | 74.77 | 83.40 | * | 61.64 |
| Ring D | 104.07 | 74.41 | 74.81 | 83.50 | * | 61.66 |
| Ring E | 104.09 | 74.41 | 74.81 | 83.48 | * | 61.64 |
| Ring F | 104.11 | 74.44 | 74.77 | 83.37 | * | 61.59 |
| Ring G | 104.09 | 74.27 | 74.76 | 83.60 | 74.17 | 61.82 |

*non-assignable signals: 2 × 74.01 and 2 × 73.99 (lack of C—H correlation)

| Fragment | H-7 | H-8 | H-9 |
|---|---|---|---|
| side chain | 3.058 | 3.382 | 3.805 |

8

EXAMPLE 3

S-(3-N,N-Bis(diphenylphosphinomethyl) aminopropyl)-$6^A$-desoxy-$6^A$-thio-β-cyclodextrin

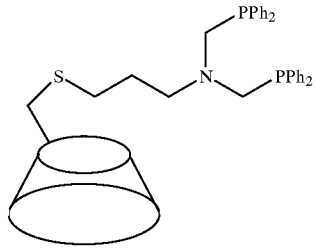

S-(2-Aminopropyl)-$6^A$-desoxy-$6^A$-thio-β-cyclodextrin:

The phthalimido protected compound is obtained by nucleophilic substitution of 6-desoxy-6-p-toluenesulfonyl-β-cyclodextrin with N-(3-mercapto)propylphthalimide and cesium carbonate as a base. DMF is used as the solvent (80° C., 24 h). Hydrazinolysis and precipitation with absolute ethanol yield a raw product which is purified by recrystallization from methanol/water. Yield: 89% (based on the cyclodextrin tosylate employed).

S-(3-N,N-Bis(diphenylphosphinomethyl)aminopropyl)-$6^A$-desoxy-$6^A$-thio-β-cyclodextrin:

2.46 g (8.7 mmol) of bis(hydroxymethyl) diphenylphosphonium chloride and 3.5 g (2.9 mmol) of S-(3-aminopropyl)-$6^A$-desoxy-$6^A$-thio-β-cyclodextrin are dissolved in a mixture of 15 ml of water and 30 ml of methanol. After the addition of 1.1 ml (7.9 mmol) of triethylamine, the mixture becomes cloudy. It is then refluxed for two hours. A white solid precipitates upon cooling. Processing and purification are performed by analogy with Example 2. Yield: 3.92 g (2.5 mmol), 86%. $^{31}$P NMR (100 MHz, $d_6$-DMSO): δ=−27.20 ppm. MS (ESI/pos. in MeOH, $H_2O$): m/z=1604 [M+H]$^+$.

EA: $C_{71}H_{99}N_1O_{34}P_2S_1.3H_2O$: MW (1657.52)

| | | | | |
|---|---|---|---|---|
| calc.: | C 51.42 | H 6.38 | N 0.84 | P 3.73 |
| found: | C 51.40 | H 6.54 | N 0.67 | P 3.75 |

EXAMPLE 4

S-(4-N,N-Bis(diphenylphosphinomethyl) aminobutyl)-$6^A$-desoxy-$6^A$-thio-β-cyclodextrin

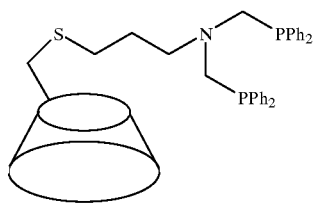

S-(4-Aminobutyl)-$6^A$-desoxy-$6^A$-thio-β-cyclodextrin:

The phthalimido protected compound is obtained by nucleophilic substitution of 6-desoxy-6-p-toluenesulfonyl-β-cyclodextrin with N-(4-mercapto)butylphthalimide and cesium carbonate as a base. DMF is used as the solvent (80° C., 24 h). Hydrazinolysis and precipitation with absolute ethanol yield a raw product which is purified by recrystallization from methanol/water. Yield: 77% (based on the cyclodextrin tosylate employed).

S-(4-N,N-Bis(diphenylphosphinomethyl)aminobutyl)-$6^A$-desoxy-$6^A$-thio-β-cyclodextrin:

1.0 g (3.5 mmol) of bis(hydroxymethyl) diphenylphosphonium chloride and 2.0 g (1.23 mmol) of S-(4-aminobutyl)-$6^A$-desoxy-$6^A$-thio-β-cyclodextrin are dissolved in a mixture of 10 ml of water and 30 ml of methanol. After the addition of 0.9 ml (6.4 mmol) of triethylamine, the mixture becomes cloudy. It is then refluxed for two hours. A white solid precipitates upon cooling. Processing and purification are performed by analogy with Example 2. Yield: 1.34 g (0.83 mmol), 67%. $^{31}$P NMR (100 MHz, $d_6$-DMSO): δ=−27.37 ppm. MS (ESI/pos. in MeOH, $H_2O$): m/z=1618 $[M+H]^+$ 100%.

EA: $C_{72}H_{101}N_1O_{34}P_2S_1 \cdot 2H_2O$: MW (1653.56)

| calc.: | C 52.25 | H 6.40 | N 0.85 | P 3.75 |
| --- | --- | --- | --- | --- |
| found: | C 52.25 | H 6.13 | N 0.84 | P 3.31 |

EXAMPLE 5

$6^A$-N,N-Bis(diphenylphosphinomethyl)amino-$6^A$-desoxyper(O-methyl)-β-cyclodextrin

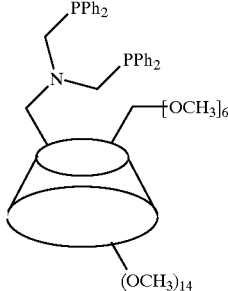

$6^A$-Azido-$6^A$-desoxyper(O-methyl)-β-cyclodextrin:

This is obtained by methylation of $6^A$-azido-$6^A$-desoxy-β-cyclodextrin with methyliodide in DMSO and anhydrous sodium hydroxide as a base. Yield: 94%. In the HPLC, the product exhibits a purity of >92%.

IR: v/cm$^{-1}$ (KBr): 2101 (ss, $N_3$)

$6^A$-Amino-$6^A$-desoxyper(O-methyl)-β-cyclodextrin:

This is obtained by reduction of $6^A$-azido-$6^A$-desoxyper(O-methyl)-β-cyclodextrin with sodium borohydride in boiling isopropanol. The reaction is monitored by IR. Yield: 96%. In the HPLC, the product exhibits a purity of >92%.

$6^A$-N,N-Bis(diphenylphosphinomethyl)amino-$6^A$-desoxyper(O-methyl)-β-cyclodextrin:

1.7 g (6.0 mmol) of bis(hydroxymethyl) diphenylphosphonium chloride and 4.0 g (2.8 mmol) of $6^A$-amino-$6^A$-desoxyper(O-methyl)-β-cyclodextrin are dissolved in a mixture of 40 ml of water and 40 ml of methanol. After the addition of 1.2 ml (8.6 mmol) of triethylamine, the mixture becomes cloudy. It is then refluxed for two hours whereupon a second phase is formed which settles. After cooling, the reaction mixture is extracted three times with 20 ml of dichloromethane and dried with a little magnesium sulfate. The solvent is evaporated in vacuo. The residue is taken up in boiling hexane, and the solution is filtered. At 0° C., the product reprecipitates as an oil. Drying under diffusion pump vacuum at 80° C. yields a hard colorless foam. The compound thus obtained is analytically pure. Yield: 4.79 g (2.6 mmol), 93%. $^1$H NMR (300 MHz, CDCl$_3$): δ=3.05 ppm (dd, $^3$J=3.3 Hz, $^3$J=9.6 Hz, 7H, H-2), 3.20–3.69 ppm (m, ~97H, H-3, H-4, H-5, H-6, OCH$_3$, NH$_2$), 4.93–5.01 ppm (m, 6H, H-1$^{B,C,D,E,F,G}$), 5.04 ppm (d, 1H, $^3$J=3.5 Hz, H-1$^A$). $^{31}$P NMR (100 MHz, CD$_2$Cl$_2$): δ=−29.00 ppm. MS (ESI/pos. in CH$_3$OH, H$_2$O): m/z=1848 ([M+K]$^+$, 28%), 1832 ([M+Na]$^+$, 100%), 1810 ([M+H]$^+$, 30%).

EA: $C_{88}H_{133}N_1P_2O_{34}$: MW (1809.818)

| calc.: | C 58.35 | H 7.41 | N 0.77 | P 3.42 |
| --- | --- | --- | --- | --- |
| found: | C 58.32 | H 7.33 | N 0.75 | P 3.47 |

EXAMPLE 6

$6^A$-N,N-Bis(diphenylphosphinomethyl)aminohepta(O-2,O-3-dimethyl)-$6^A$-desoxy-β-cyclodextrin

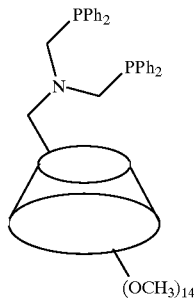

$6^A$-Azidohexakis(O-6-tert-butyldimethylsilyl)-$6^A$-desoxy-β-cyclodextrin:

This is obtained by the reaction of $6^A$-azido-$6^A$-desoxy-β-cyclodextrin with tert-butyldimethylchlorosilane in pyridine. The product is purified by column chromatography (silica gel, ethanol/ethyl acetate/water). Yield: 76%.

$6^A$-Azidohexakis(O-6-tert-butyldimethylsilyl)heptakis(O-2,O-3-dimethyl)-$6^A$-desoxy-β-cyclodextrin:

This is obtained by the methylation of $6^A$-azidohexakis(O-6-tert-butyldimethylsilyl)-$6^A$-desoxy-β-cyclodextrin with sodium hydride and methyl iodide in THF. The product is again purified by column chromatography (silica gel, methylene chloride/methanol). Yield: 95%.

$6^A$-Azidoheptakis(O-2,O-3-dimethyl)-$6^A$-desoxy-β-cyclodextrin:

The desilylation is achieved by refluxing $6^A$-azidohexakis(O-6-tert-butyldimethylsilyl)heptakis(O-2,O-3-dimethyl)-$6^A$-desoxy-β-cyclodextrin with pyridinium tosylate in absolute ethanol. A mixed-bed ion-exchanger is used for the processing. Yield: 96%.

$6^A$-Aminoheptakis(O-2,O-3-dimethyl)-$6^A$-desoxy-β-cyclodextrin:

This is obtained by catalytic reduction of $6^A$-Azidoheptakis(O-2,O-3-dimethyl)-$6^A$-desoxy-β-cyclodextrin with platinum dioxide and molecular hydrogen (1 atm). The reaction is monitored by IR. The processing yields a slightly yellowish foam in 75% yield.

$6^A$-N,N-Bis(diphenylphosphinomethyl)aminoheptakis(O-2,O-3-dimethyl)-$6^A$-desoxy-β-cyclodextrin:

1.0 g (3.3 mmol) of bis(hydroxymethyl) diphenylphosphonium chloride and 1.8 g (1.35 mmol) of $6^A$-amino-$6^A$-desoxyheptakis(O-2,O-3-dimethyl)-β-cyclodextrin are dissolved in a mixture of 12 ml of water and 12 ml of methanol. After the addition of 0.7 ml (5.0 mmol) of triethylamine, the mixture becomes cloudy. It is then refluxed for two hours upon which a white emulsion is formed. After cooling, the reaction mixture is extracted three times with 20 ml of dichloromethane and dried with a little magnesium sulfate. The solvent is evaporated in vacuo. The residue is taken up in hexane/diethyl ether=1:1, and the solution is filtered. At 0° C., the product reprecipitates as an oil. Drying under diffusion pump vacuum at 80° C. yields a hard yellowish foam. The compound thus obtained is analytically pure. Yield: 1.73 g (1.0 mmol), 74%. $^{31}$P NMR (100 MHz, $CD_2Cl_2$): δ=−28.70 ppm. MS (ESI/pos. in $CH_3OH$, $H_2O$): m/z=1765 ([M+K]$^+$, 5%), 1749 ([M+Na]$^+$, 100%), 1727 ([M+H]$^+$, 55%).

EA: $C_{82}H_{121}N_1P_2O_{34}$: MW (1725.72)

| | | | | |
|---|---|---|---|---|
| calc.: | C 57.02 | H 7.07 | N 0.81 | P 3.59 |
| found: | C 56.71 | H 7.33 | N 0.73 | P 3.41 |

EXAMPLE 7

6$^A$N-Bis(diphenylphosphinomethyl)aminohepta(O-methyl)-6$^A$-desoxy-β-cyclodextrin

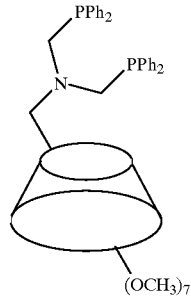

6$^A$Azidohexakis(O-6-tert-butyldimethylsilyl)hept(O-methyl)-6$^A$-desoxy-β-cyclodextrin:

This is obtained by carefulley methylating 6$^A$-azidohexakis(O-6-tert-butyldimethylsily)-6$^A$-desoxy-β-cyclodextrin with sodium hydride and methyl iodide in THF. Purification is again performed by column chromatography (silica gel, methylene chloride/methanol). Yield: 83%.

6$^A$-Azidohepta(O-methyl)-6$^A$-desoxy-β-cyclodextrin:

The desilylation is achieved by refluxing 6$^A$-azidohexakis (O-6-tert-butyldimethylsilyl)hepta(O-methyl)-6$^A$-desoxy-β-cyclodextrin with pyridinium tosylate in absolute ethanol. A mixed-bed ion-ex-changer is used for the processing. Yield: 77%.

6$^A$-Aminohepta(O-methyl)-6$^A$-desoxy-β-cyclodextrin:

This is obtained by catalytic reduction of 6$^A$-Azidohepta (O-methyl)-6$^A$-desoxy-β-cyclodextrin with platinum dioide and molecular hydrogen (1 atm). The reaction is monitored by IR. The processing yields a slightly yellowish foam in 98% yield.

6$^A$-N,N-Bis(diphenylphosphinomethyl)aminohepta(O-methyl)-6$^A$-desoxy-β-cyclodextrin:

1.2 g (4.2 mmol) of bis(hydroxymethyl) diphenylphosphonium chloride and 2.1 g (1.7 mmol) of 6$^A$-amino-6$^A$-desoxyhepta(O-methyl)-β-cyclodextrin are dissolved in a mixture of 15 ml of water and 15 ml of methanol. After the addition of 0.8 ml (5.8 mmol) of triethylamine, the mixture becomes cloudy. It is then refluxed for two hours upon which a white emulsion is formed. After cooling, the reaction mixture is extracted three times with 20 ml of dichloromethane and dried with a little magnesium sulfate. The solvent is evaporated in vacuo. The residue is taken up in hexane/diethyl ether=1:4, and the solution is filtered. At 0° C., the product reprecipitates as an oil. Drying under diffusion pump vacuum at 80° C. yields a hard yellowish foam. The compound thus obtained is analytically pure. Yield: 1.2 g (0.74 mmol), 44%. $^{31}$P NMR (100 MHz, d$_6$-DMSO): δ=−28.70 ppm. MS (ESI/pos. in $CH_3OH$, $H_2O$): m/z=1668 ([M+K]$^+$, 5%), 1651 ([M+Na]$^+$, 17%), 1629 ([M+H]$^+$, 25%).

EXAMPLE 8

[S-(2-N,N-Bis(diphenylphosphinomethyl) aminoethyl)-6$^A$-desoxy-6$^A$-thio-β-cyclodextrin][η$^2$, η$^2$-cycloocta-1,5-diene]rhodium(I) Tetrafluoroborate Under argon atmosphere, 1.0 g (0.62 mmol) of S-(2-N, N-bis(diphenylphosphinomethyl)aminoethyl)-6$^A$-desoxy-6$^A$-thio-β-cyclodextrin (the ligand from Example 2) and 251 mg (0.62 mmol) of bis-(η$^2$,η$^2$-cycloocta-1,5-diene)rhodium (I) tetrafluoroborate are suspended in a mixture of 30 ml of methanol and 10 ml of dichloromethane which is stirred at room temperature for 24 h. All volatiles are removed under vacuum. The residue is extracted several times with hot dichloromethane. Drying under high vacuum yields an orange powder. Yield 1.08 g (0.57 mmol), 92%. $^{31}$P NMR (600 MHz, d$_6$-DMSO): δ=+8.05 ppm, $^1J_{RhP}$=143 Hz. MS (ESI/pos. in $CH_3OH$, $H_2O$): m/z=1818 ([M−Cl+H$_2$O]$^+$, 20%), 1800 ([M−Cl]$^+$, 100%).

EA: $C_{78}H_{109}N_1P_2O_{34}S_1B_1F_4Rh_1$: MW (1887.51)

| | | | | |
|---|---|---|---|---|
| calc. : | C 49.49 | H 5.82 | Rh 5.45 | P 3.28 |
| found: | C 49.23 | H 5.71 | Rh 4.75 | P 3.66 |

EXAMPLE 9

[S-(2-N,N-Bis(diphenylphosphinomethyl) aminoethyl)-6$^A$-desoxy-6$^A$-thio-β-cyclodextrin] chloro(η$^6$-cymol)-ruthenium(II) Chloride Under argon atmosphere, 1.0 g (0.62 mmol) of S-(2-N, N-bis(diphenylphosphinomethyl)aminoethyl)-6$^A$-desoxy-6$^A$-thio-β-cyclodextrin (the ligand from Example 2) and 215 mg (0.35 mmol) of di-μ-chlorodichlorobis[(p-cymol) ruthenium(II)] are suspended in a mixture of 30 ml of methanol and 10 ml of dichloromethane which is stirred at room temperature for 24 h. All volatiles are removed under vacuum. The residue is extracted several times with hot dichloromethane. Drying under high vacuum yields a light-red powder. Yield 1.12 g (0.59 mmol), 95%. $^{31}$P NMR (100 MHz, d$_6$-DMSO): δ=+21.21 ppm. MS (FAB/pos., matrix: glycerol): m/z=1861 ([M−Cl]$^+$, 100%).

EA: $C_{80}H_{111}N_1P_2O_{34}S_1Ru_1Cl_2$: MW (1895.46)

| | | | | |
|---|---|---|---|---|
| calc.: | C 50.65 | H 5.90 | Ru 5.90 | P 3.27 |
| found: | C 48.99 | H 5.88 | Ru 6.23 | P 3.11 |

EXAMPLE 10

[S-(2-N,N-Bis(diphenylphosphinomethyl) aminoethyl)-6$^A$-desoxy-6$^A$-thio-β-cyclodextrin] palladium Dichloride Under argon atmosphere, 1.0 g (0.62 mmol) of S-(2-N, N-bis(diphenylphosphinomethyl)aminoethyl)-6$^A$-desoxy- $6^A$-thio-β-cyclodextrin (the ligand from Example 2) and 250 mg (0.87 mmol) of (1,5-cyclooctadiene)palladium dichloride are suspended in 20 ml of methanol which is stirred at room temperature for 24 h. The residue is isolated and washed five times with 10 ml of methanol. Drying under high vacuum at 50° C. yields an air-stable yellow powder. Yield 878 mg (0.5 mmol), 80%. $^{31}$P NMR (100 MHz, $d_6$-DMSO): δ=+8.1 ppm. MS (ESI/pos. in $CH_3OH$, $H_2O$): m/z=1788 ([M+Na]$^+$, 60%), 1730 ([M−Cl]$^+$, 100%).

EA: $C_{70}H_{97}N_1P_2O_{34}S_1Pd_1Cl_2$: MW (1766.32)

| | | | | |
|---|---|---|---|---|
| calc.: | C 47.58 | H 5.54 | Pd 6.00 | P 3.51 |
| found: | C 47.31 | H 5.72 | Pd 6.17 | P 3.49 |

EXAMPLE 11

Hydroformylation of 1-octene with the Ligand from Example 1

In a 50 ml Schlenk flask, $2.4·10^{-5}$ mol of the ligand (i.e., $6^A$-N,N-bis(diphenylphosphinomethyl)amino-$6^A$-desoxy-β-cyclodextrin) is weighed and dissolved in 5 ml of DMF. To this is added $2·10^{-5}$ mol of Rh(cod)$_2$BF$_4$ (1 ml, stock solution 0.02 M in DMF), and the mixture is stirred for 10 min. Water is added to a total volume of 20 ml. To this is added 10 ml of 1-octene. The thus prepared catalyst charge is transferred with a syphon pipe with argon countercurrent to an autoclave equipped with a Teflon insert and stirring bar which had previously been heated at 80° C. in a drying oven to remove moisture and filled with argon. The autoclave is closed, and synthesis gas is added at 100 bar. With maximum stirring, the contents are heated to the desired reaction temperature, and the autoclave is maintained at 60° C. during the reaction. After 18 h, the reaction is stopped, the increased pressure of synthesis gas is released, and the phases are separated in a separatory funnel. The organic phase is dried over a little magnesium sulfate and filtered. The conversion and the selectivities to the products are determined by $^1$H NMR (200 MHz, CDCl$_3$). The aldehyde signals are used as a diagnostic sign. The structure of the products is confirmed by GC/MS. Isomerization and hydrogenation products are identified by gas chromatography.

Conversion: 95% (turnover number=3011), aldehyde selectivity: >99%, n/iso=3.3.

EXAMPLE 12

Hydroformylation of 1-octene with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Conversion: 100% (turnover number=3170), aldehyde selectivity: >99%, n/iso=3.0.

EXAMPLE 13

Hydroformylation of 1-octene with the same procedure as described in Example 11, but with only water and without DMF as a cosolvent.

Conversion: 95% (turnover number=3011), aldehyde selectivity: >99%, n/iso=3.0.

EXAMPLE 14

Hydroformylation of 1-octene with the same procedure as described in Example 10, but using the ligand from Example 3 (S-(3-N,N-bis(diphenylphosphinomethyl)aminopropyl)-$6^A$-desoxy-$6^A$-thio-β-cyclodextrin).

Conversion: 100% (turnover number=3170), aldehyde selectivity: >99%, n/iso=2.25.

EXAMPLE 15

Hydroformylation of 1-octene with the same procedure as described in Example 10, but using the ligand from Example 4 (S-(4-N,N-bis(diphenylphosphinomethyl)aminobutyl-$6^A$-desoxy-$6^A$-thio-β-cyclodextrin).

Conversion: 100% (turnover number=3170), aldehyde selectivity: >99%, n/iso=2.0.

EXAMPLE 16

Hydroformylation of 1-octene with the same procedure as described in Example 10, but using the ligand from Example 5 ($6^A$-N,N-bis(diphenylphosphinomethyl)amino-$6^A$-desoxyper(O-methyl)-β-cyclodextrin).

Conversion: 100% (turnover number=3170), aldehyde selectivity: >99%, n/iso=1.91.

EXAMPLE 17

Hydroformylation of 1-octene with the same procedure as described in Example 10, but using the ligand from Example 6 ($6^A$-N,N-bis(diphenylphosphinomethyl)aminoheptakis(O-2,O-3-dimethyl)-$6^A$-desoxy-β-cyclodextrin).

Conversion: 100% (turnover number=3170), aldehyde selectivity: >99%, n/iso=2.7.

EXAMPLE 18

Hydroformylation of 1-octene with the same procedure as described in Example 10, but using the ligand from Example 7 ($6^A$-N,N-bis(diphenylphosphinomethyl)aminohepta(O-methyl)-$6^A$-desoxy-β-cyclodextrin).

Conversion: 100% (turnover number=3170), aldehyde selectivity: >99%, n/iso=3.0.

EXAMPLE 19

Hydroformylation of 10 ml of 1-hexene with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Conversion: 81% (turnover number=3246), aldehyde selectivity: >99%, n/iso=3.1.

EXAMPLE 20

Hydroformylation of 10 ml of 1-decene with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Conversion: 89% (turnover number=2342), aldehyde selectivity: >99%, n/iso=3.2.

EXAMPLE 21

Hydroformylation of 10 ml of 1-dodecene with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Conversion: 94% (turnover number=2139), aldehyde selectivity: >99%, n/iso=3.4.

EXAMPLE 22

Hydroformylation of 10 ml of vinylcyclohexane with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Reaction time: 18 h: Conversion: 78% (turnover number=2848), aldehyde selectivity: >99%, n/iso=5.6.

Reaction time: 24 h: Conversion: 98% (turnover number=3570), aldehyde selectivity: >99%, n/iso=5.6.

EXAMPLE 23

Hydroformylation of 10 ml of vinylcyclooctane with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Reaction time: 18 h: Conversion: 57% (turnover number=1748), aldehyde selectivity: >99%, n/iso=7.1.

Reaction time: 70 h: Conversion: 98% (turnover number=3015), aldehyde selectivity: >99%, n/iso=7.0.

EXAMPLE 24

Hydroformylation of 10 ml of 3,3-dimethylbutene (neohexene) with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Reaction time: 18 h: Conversion: 62% (turnover number=2404), in a Two-Phase System aldehyde selectivity: >99%, n/iso=19.6.

Reaction time: 70 h: Conversion: 99% (turnover number=3840), aldehyde selectivity: >99%, n/iso=20.3.

EXAMPLE 25

Hydroformylation of 10 ml of methylenecyclohexane with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Reaction time: 70 h: Conversion: 45% (turnover number=1872), aldehyde selectivity: >99%, 100% n-aldehyde.

Reaction time: 150 h: Conversion: 89% (turnover number=3702), aldehyde selectivity: >99%, 100% n-aldehyde.

EXAMPLE 26

Hydroformylation of 10 ml of 2-methyl-1-pentene with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Reaction time: 70 h: Conversion: 29% (turnover number=1169), aldehyde selectivity: >99%, 100% n-aldehyde.

Reaction time: 150 h: Conversion: 47% (turnover number=1895), aldehyde selectivity: >99%, 100% n-aldehyde.

EXAMPLE 27

Hydroformylation of 10 ml of cis-3-hexene with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Reaction time: 70 h: Conversion: 89% (turnover number=2848), aldehyde selectivity: >99%. Products: 79% 2-ethylpentanal, 7% 2-methylhexanal, 3% n-heptanal.

EXAMPLE 28

Hydroformylation of 10 ml of trans-3-hexene with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Reaction time: 70 h: Conversion: 94% (turnover number=3008), aldehyde selectivity: >99%. Products: 90% 2-ethylpentanal, 4% 2-methylhexanal, 0% n-heptanal.

EXAMPLE 29

Hydroformylation of 10 ml of methyl oleate with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Reaction time 70 h and reaction temperature 80° C.: Conversion: 21% (turnover number=311); reaction time 200 h and reaction temperature 80° C.: Conversion: 45% (turnover number=666), each with an aldehyde selectivity of >96%.

EXAMPLE 30

Hydroformylation of 10 ml of cyclopentene with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Reaction time: 18 h: Conversion: 67% (turnover number=3806), aldehyde selectivity: >99%.

Reaction time: 70 h: Conversion: 100% (turnover number=5681), aldehyde selectivity: >99%.

EXAMPLE 31

Hydroformylation of 10 ml of cyclohexene with the same procedure as described in Example 10, but using the ligand from Example 2 (S-(2-N,N-bis(diphenylphosphinomethyl)aminoethyl)-$6^A$-desoxy-$6^A$-thio-β-cyclodextrin). Reaction temperature: 80° C.

Reaction time: 18 h: Conversion: 12% (turnover number=480), aldehyde selectivity: >99%.

Reaction time: 70 h: Conversion: 47% (turnover number=1880), aldehyde selectivity: >99%.

EXAMPLE 32

Hydroformylation of 10 ml of cis-cyclooctene with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Reaction time: 70 h: Conversion: 66% (turnover number=2541), aldehyde selectivity: >99%.

EXAMPLE 33

Hydroformylation of 10 ml of cis-cyclododecene with the same procedure as described in Example 10, but using the ligand from Example 2 (S-(2-N,N-bis(diphenylphosphinomethyl)aminoethyl)-$6^A$-desoxy-$6^A$-thio-β-cyclodextrin).

Reaction time: 70 h: Conversion: 22% (turnover number=556), aldehyde selectivity: >99%.

EXAMPLE 34

Hydroformylation of 10 ml of 4-vinylcyclohexene with the same procedure as described in Example 10, but using the ligand from Example 2 (S-(2-N,N-bis(diphenylphosphinomethyl)aminoethyl)-6$^A$-desoxy-6$^A$-thio-β-cyclodextrin).

Reaction time: 70 h: Conversion: 100% (turnover number=3845), aldehyde selectivity: >99%, n/iso=5.6.

Only the exocyclic double bond is selectively converted.

EXAMPLE 35

Hydroformylation of 10 ml of 1-methylcyclopentene with the same procedure as described in Example 10, but using the ligand from Example 2 (S-(2-N,N-bis(diphenylphosphinomethyl)aminoethyl)-6$^A$-desoxy-6$^A$-thio-β-cyclodextrin). Reaction temperature: 70° C.

Reaction time: 70 h: Conversion: 49% (turnover number=2352), aldehyde selectivity: >99%.

Reaction time: 150 h: Conversion: 98% (turnover number=4700), aldehyde selectivity: >99%.

Product: 2-methylcyclopentenecarbaldehyde.

EXAMPLE 36

Hydroformylation of 10 ml of styrene with the same procedure as described in Example 10, but using the ligand from Example 2 (S-(2-N,N-bis(diphenylphosphinomethyl)aminoethyl)-6$^A$-desoxy-6$^A$-thio-β-cyclodextrin).

Reaction time: 18 h: Conversion: 73% (turnover number=3175), aldehyde selectivity: >99%, n/iso=0.124.

EXAMPLE 37

Hydroformylation of 10 ml each of 1-octene with the same procedure as described in Example 10, but using the ligand from Example 2 (S-(2-N,N-bis(diphenylphosphinomethyl)aminoethyl)-6$^A$-desoxy-6$^A$-thio-β-cyclodextrin). However, the autoclave is opened under argon, and the catalyst phase is again transferred to a catalytic process.

| catalyst charge | conversion (TON) | reaction time | aldehyde selectivity | n/iso |
|---|---|---|---|---|
| new | 100% (3172) | 18 h | >99% | 3.0 |
| 1st recycling | 93% (2950) | 18 h | >99% | 3.0 |
| 2nd recycling | 77% (2441) | 18 h | >99% | 2.8 |

EXAMPLE 39

Comparison with TPPTS

Hydroformylation of 10 ml each of 1-octene with the same procedure as described in Example 10. The reaction is stopped after eight hours already. In the case using TPPTS, a tenfold excess of ligand (2.4·10$^{-4}$ mol) is used.

| ligand | conversion (TON) | t | T | n/iso |
|---|---|---|---|---|
| TPPTS | 0.43% (14) | 8 h | 120° C. | 8.1 |
| Example 2 | 66% (2092) | 8 h | 60° C. | 3.0 |

The S-(2-N,N-bis(diphenylphosphinomethyl)aminoethyl)-6$^A$-desoxy-6$^A$-thio-β-cyclodextrin/rhodium system exhibits an activity in hydroformylation which is 153 times as high as that of the TPPTS/Rh system.

What is claimed is:

1. A β-cyclodextrin modified diphosphine comprising a bis (diarylphosphinomethyl) amino or bis (dialkylphosphinomethyl) amino moiety bonded indirectly through a spacer or directly to the 6-position of β-cyclodextrin or an alkylated form of β-cyclodextrin.

2. A transition metal complex comprising a β-cyclodextrin modified diphosphine according to claim 1 and a Periodic Table group VIII metal salt bound thereto.

3. A process for the hydroformylation of an olefin selected from the group consisting of 1-alkenes, 1,1-disubstituted alkenes, internal disubstituted alkenes, cycloalkenes and trisubstituted alkenes, said process comprising reacting said olefin with CO/H$_2$ in a two-phase system in the presence of a catalyst comprising a transition metal complex according to claim 2, wherein a first phase of said two-phase system comprises water and said catalyst, and a second phase of said two-phase system comprises said olefin or said olefin dissolved in an organic solvent.

4. The process according to claim 3, wherein said first phase further comprises dimethylformamide.

* * * * *